US012780772B2

(12) United States Patent
Bae et al.

(10) Patent No.: US 12,780,772 B2
(45) Date of Patent: Nov. 3, 2026

(54) TANDEM CATALYST FOR SYNTHESIZING METHYL ACETATE FROM CARBON DIOXIDE, METHOD FOR PREPARING SAME, AND METHOD FOR PREPARING METHYL ACETATE USING SAME

(71) Applicant: RESEARCH & BUSINESS FOUNDATION SUNGKYUNKWAN UNIVERSITY, Suwon-si (KR)

(72) Inventors: Jong Wook Bae, Suwon-si (KR); Xu Wang, Suwon-si (KR); So Yun Jeong, Suwon-si (KR); Eun Jeong Kim, Jeju-si (KR); Zafar Faisal, Suwon-si (KR); Ali Mansoor, Suwon-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 499 days.

(21) Appl. No.: 18/383,156

(22) Filed: Oct. 24, 2023

(65) Prior Publication Data

US 2024/0132437 A1 Apr. 25, 2024
US 2024/0228420 A9 Jul. 11, 2024

(30) Foreign Application Priority Data

Oct. 24, 2022 (KR) ........................ 10-2022-0137520

(51) Int. Cl.
*C07C 67/00* (2006.01)
*B01J 21/08* (2006.01)
(Continued)

(52) U.S. Cl.
CPC ............... *C07C 67/00* (2013.01); *B01J 21/08* (2013.01); *B01J 23/80* (2013.01); *B01J 29/65* (2013.01); *B01J 29/68* (2013.01); *B01J 35/19* (2024.01); *B01J 35/40* (2024.01); *B01J 35/615* (2024.01); *B01J 35/633* (2024.01); *B01J 37/0018* (2013.01); *B01J 37/082* (2013.01);
(Continued)

(58) Field of Classification Search
None
See application file for complete search history.

(56) References Cited

U.S. PATENT DOCUMENTS 9,546,120 B2 1/2017 Bristow
2017/0072388 A1 3/2017 Reule et al.
2020/0239401 A1 * 7/2020 Liu .......................... B01J 8/065

FOREIGN PATENT DOCUMENTS

CN 114797963 A * 7/2022 ............. C07C 51/10
KR 10-1921417 B1 11/2018

OTHER PUBLICATIONS

Translation of Nariyasu (Cn 114797963A, published on Jul. 29, 2022), obtained Apr. 2026 (Year: 2026).*

(Continued)

*Primary Examiner* — Amy C Bonaparte
(74) *Attorney, Agent, or Firm* — LEX IP MEISTER, PLLC

(57) ABSTRACT

Disclosed are a tandem catalyst for synthesizing methyl acetate from carbon dioxide, a method for preparing the same, and a method for preparing methyl acetate using the same. The tandem catalyst of the present invention includes a first catalyst having a core-shell structure including a composite metal oxide core and a silica shell surrounding a surface of the composite metal oxide core, and a second catalyst including nano-ferrierite (N-FER) zeolite.

17 Claims, 6 Drawing Sheets

(51) Int. Cl.

| | |
|---|---|
| ***B01J 23/80*** | (2006.01) |
| ***B01J 29/65*** | (2006.01) |
| ***B01J 29/68*** | (2006.01) |
| ***B01J 35/00*** | (2024.01) |
| ***B01J 35/40*** | (2024.01) |
| ***B01J 35/61*** | (2024.01) |
| ***B01J 35/63*** | (2024.01) |
| ***B01J 37/00*** | (2006.01) |
| ***B01J 37/08*** | (2006.01) |
| ***B01J 37/10*** | (2006.01) |
| ***B01J 37/18*** | (2006.01) |
| ***B01J 37/30*** | (2006.01) |
| ***C01B 39/44*** | (2006.01) |

(52) U.S. Cl.

CPC ............... *B01J 37/10* (2013.01); *B01J 37/18* (2013.01); *B01J 37/30* (2013.01); *C01B 39/445* (2013.01)

(56) References Cited

OTHER PUBLICATIONS

Translation of Lee (KR20140078471A, published on Jun. 25, 2014), obtained Apr. 2026 (Year: 2026).*

Yang ("Core-shell structure Cu@m-SiO2 and Cu/ZnO@m-SiO2 catalysts for methanol synthesis from CO2 hydrogenation" Catalysis Communications, 84, 2016, p. 56) (Year: 2016).*

* cited by examiner

【Fig. 1】
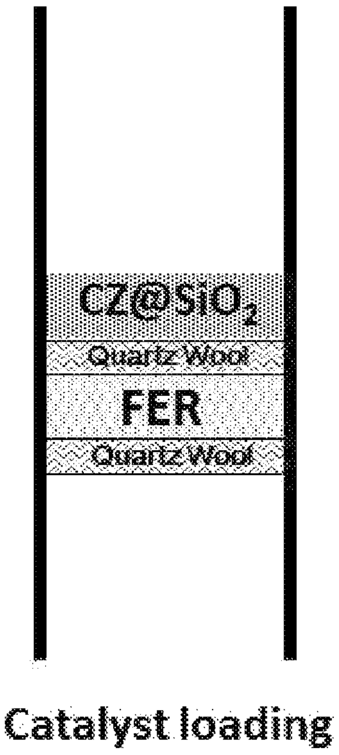

【Fig. 2】
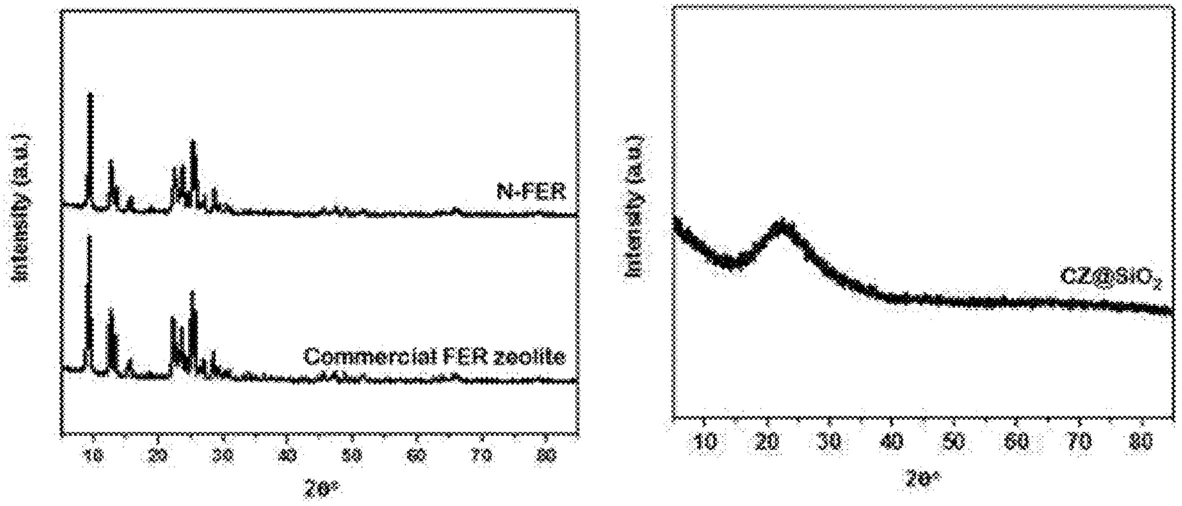

【Fig. 3】
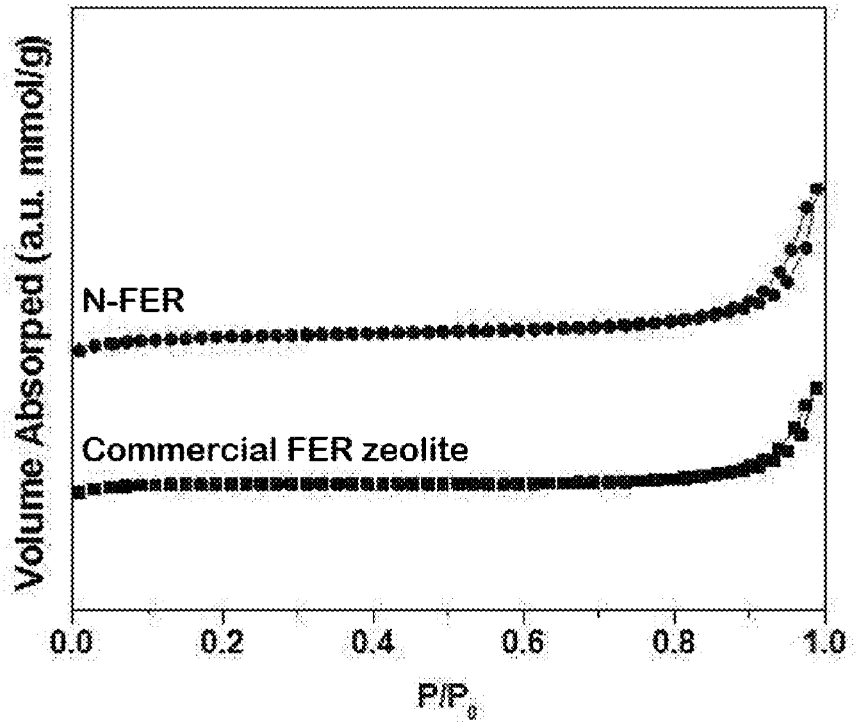

【Fig. 4】
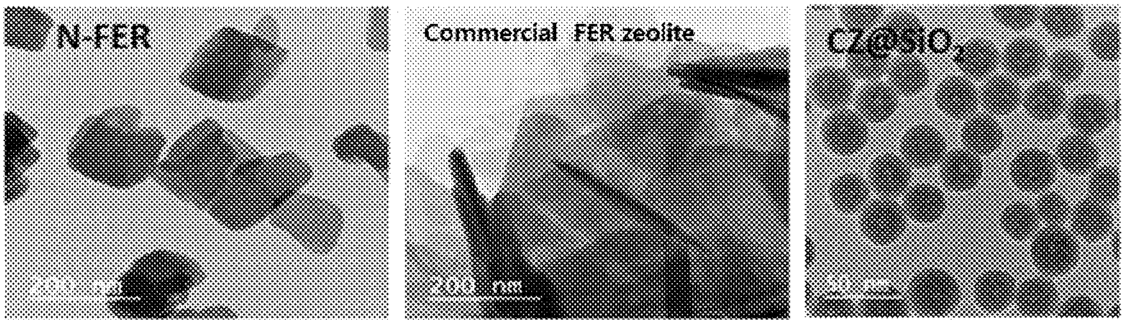

【Fig. 5】
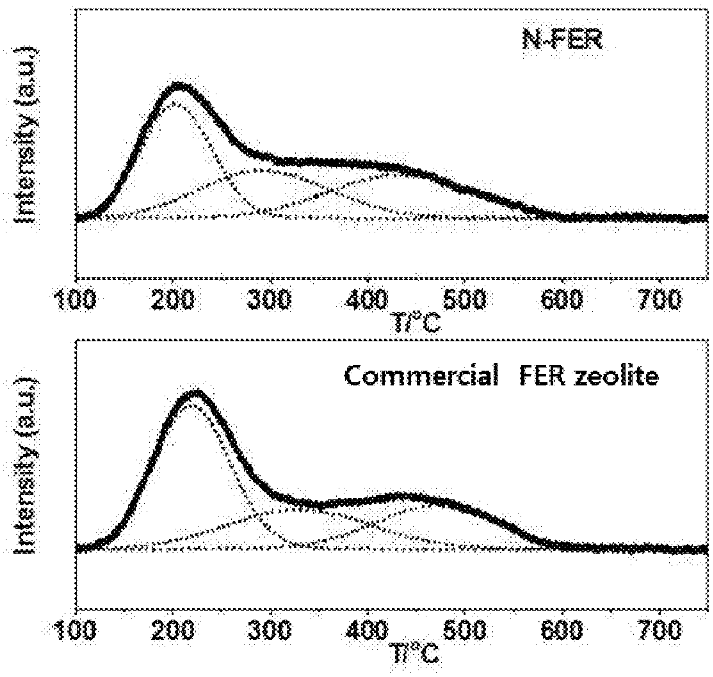

【Fig. 6】
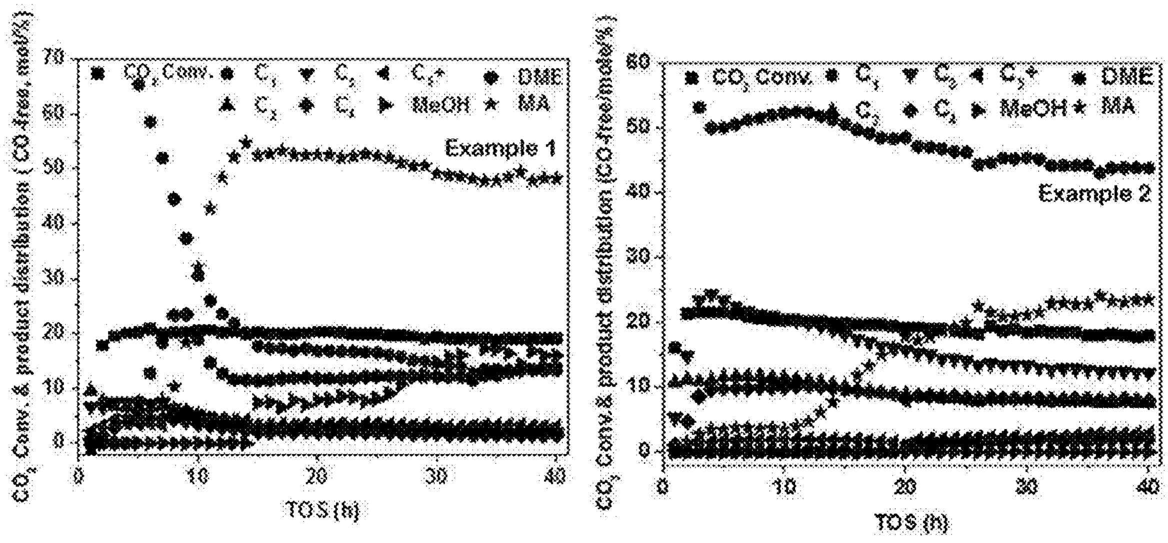

TANDEM CATALYST FOR SYNTHESIZING METHYL ACETATE FROM CARBON DIOXIDE, METHOD FOR PREPARING SAME, AND METHOD FOR PREPARING METHYL ACETATE USING SAME

BACKGROUND OF THE INVENTION

1. Field of the Invention

The present invention relates to a catalyst, and more particularly, to a tandem catalyst for synthesizing methyl acetate from carbon dioxide, a method for preparing the same, and a method for preparing methyl acetate using the same.

2. Description of the Related Art

Direct and selective C2+ oxygenate synthesis through C1 chemistry is a very interesting theme because $CO_2$ greenhouse gas, which is the main cause of global warming, can be efficiently utilized. Methyl acetate, which is one of the most important petrochemical intermediates such as ethanol, may be synthesized through multiple catalytic processes that involve (1) methanol synthesis from CO2, (2) methanol to dimethyl ether, and (3) carbonylation of dimethyl ether with formed-CO to methyl acetate. The conventional multiple synthesis processes result in low stability (carbonylation reaction) and high energy consumption due to multiple pathways for production of each intermediate. Accordingly, reasonable yields have not been achieved through various single-step syntheses of methyl acetate from carbon dioxide have been studied.

Among the existing research results, there are no reports of successful synthesis of methyl acetate from carbon dioxide with significant productivity through a single process. There is a need to develop a catalyst capable of synthesizing methyl acetate from carbon dioxide through a single step.

SUMMARY OF THE INVENTION

One object of the present invention is to provide a tandem catalyst capable of synthesizing methyl acetate from carbon dioxide through a single step and a method for preparing the same.

Another object of the present invention is to provide a method for preparing methyl acetate using the tandem catalyst.

The tandem catalyst for synthesizing methyl acetate from carbon dioxide for the one object of the present invention includes a first catalyst including nano-ferrierite (N-FER) zeolite, and a second catalyst having a core-shell structure including a composite metal oxide core and a silica shell surrounding a surface of the composite metal oxide core.

In one embodiment, in the tandem catalyst, the weight ratio of the second catalyst/the first catalyst may be 0.1 to 2.0.

In one embodiment, the composite metal oxide core may include copper oxide (CuO) and zinc oxide (ZnO).

In one embodiment, the second catalyst may include 2 wt % to 10 wt % of copper oxide (CuO), 1 wt % to 5 wt % of zinc oxide (ZnO) and a remainder of the silica shell based on total weight.

In one embodiment, the nano-ferrierite (N-FER) zeolite may be Na-type ferrierite or H-type ferrierite, and the nano-ferrierite (N-FER) zeolite may have a Si/Al molar ratio of 10 to 20 and a BET surface area of 290 $m^2/g$ to 350 $m^2/g$.

In one embodiment, the first catalyst may have a size of 200 nm to 800 nm.

In one embodiment, the composite metal oxide core of the second catalyst may have a size of 5 nm to 10 nm, and the silica shell may have a diameter of 20 nm to 50 nm.

In addition, the method for preparing a tandem catalyst for synthesizing methyl acetate from carbon dioxide for another object of the present invention includes: a first step of preparing nano-ferrierite (N-FER) zeolite by hydrothermally synthesizing a first precursor solution containing a first silica precursor, an alumina precursor and a first organic template agent and then calcining; a second step of preparing a composite metal oxide core-silica shell by adding a second silica precursor solution to a second precursor solution containing a metal precursor and a second organic template agent and then calcining; and a third step of arranging the nano-ferrierite (N-FER) zeolite and the composite metal oxide core-silica shell in tandem.

In one embodiment, the first silica precursor may include a substance selected from silica sol, tetraethyl orthosilicate (TEOS), fumed silica, colloidal silica, silica gel, and sodium silicate, the alumina precursor may include a substance selected from aluminum oxide, kaolin, aluminum isopropoxide, aluminum nitrite, sodium aluminate, and aluminum sulfate, and the first organic template agent may include a substance selected from cetrimonium bromide, ammonium lauryl sulfate, pyridine, pyrrolidine, ethylenediamine and n-butylamine.

In one embodiment, the first silica precursor and the first organic template agent may have a molar ratio of 0.5:1 to 2:1, and the first silica precursor and the alumina precursor may have a molar ratio of 5:1 to 20:1.

In one embodiment, in the first step, the hydrothermally synthesizing may be performed at 110° C. to 180° C. for 168 hours to 504 hours, and the calcining may be performed at 450° C. to 650° C.

In one embodiment, the method after the first step may further include: performing ion exchange by dispersing the synthesized nano-ferrierite (N-FER) zeolite in an ammonium solution; and calcining the ion exchanged nano-ferrierite (N-FER) zeolite at 450° C. to 650° C.

In one embodiment, the metal precursor may include a copper precursor and a zinc precursor, the second organic template agent may include a substance selected from cetrimonium bromide (CTAB), ethylene oxide-propylene oxide-ethylene oxide copolymer (EO106PO70EO106), polyoxyethylene (10) cetyl ether (C16E10), ethylene oxide-propylene oxide-ethylene oxide copolymer (EO20PO70EO20) and polyethylene glycol hexadecyl ether ($C_{16}H_{33}(OCH_2CH_2)nOH$, n=1 to 10), and the second silica precursor solution may include a substance selected from a basic material, and silica sol, tetraethyl orthosilicate (TEOS) and fumed amorphous silica as secondary silica precursors.

In one embodiment, in the second step, the calcining may be performed at 400° C. to 600° C.

In addition, the method for preparing methyl acetate from carbon dioxide for another object of the present invention includes: arranging the tandem catalyst inside a reactor; reducing the tandem catalyst by heating the inside of the reactor; and performing a reaction by injecting gas containing carbon dioxide and hydrogen into the reactor, so that methyl acetate may be synthesized from carbon dioxide.

In one embodiment, the reaction may be performed at 200° C. to 400° C.

The tandem catalyst according to the present invention may have high methyl acetate selectivity, high $CO_2$ conversion and high stability, so that excellent catalytic performance can be exhibited. Accordingly, the tandem catalyst according to the present invention may produce methyl acetate serving as an essential intermediate in ethanol synthesis from carbon dioxide as greenhouse gas through only the single step, so that carbon neutrality can be realized. As a result, when carbon dioxide is converted to methyl acetate (MA) in the related art, a carbonylation reaction from $CO_2$ into methanol, methanol into DME, and DME and CO into MA is performed through multiple processes. However, the present invention integrates the multiple processes into one process, so that low energy consumption for producing methyl acetate (MA) can be implemented, enormous economic benefits can be obtained, and significant production for achieving carbon neutrality can be implemented by utilizing greenhouse gases.

BRIEF DESCRIPTION OF THE DRAWINGS

FIG. 1 is a view schematically showing a tandem catalyst for synthesizing methyl acetate from carbon dioxide according to one embodiment of the present invention.

FIG. 2 shows XRD analysis results on a tandem catalyst according to Example 1 of the present invention and a commercial FER zeolite catalyst.

FIG. 3 shows results on nitrogen adsorption and desorption analysis of the tandem catalyst according to Example 1 of the present invention and the commercial FER zeolite catalyst.

FIG. 4 shows transmission electron microscopy images of the tandem catalyst according to Example 1 of the present invention and the commercial FER zeolite catalyst.

FIG. 5 shows results on ammonia adsorption and desorption analysis of a nano-ferrierite zeolite catalyst synthesized according to the Example of the present invention and commercial FER zeolite.

FIG. 6 show results on a synthesis conversion reaction from carbon dioxide to methyl acetate according to one embodiment of the present invention.

DETAILED DESCRIPTION OF THE INVENTION

The terms used herein are just for the purpose of describing particular embodiments and are not intended to limit the present invention. The singular expression includes a plural expression unless the context clearly means otherwise. Herein, it will be understood that the term such as "include" or "have" is intended to designate the presence of feature, step, operation, element, component, or a combination thereof recited in the specification, which does not preclude the possibility of the presence or addition of one or more other features, steps, elements, components, or combinations thereof.

Unless otherwise defined, all terms used herein including technical or scientific terms have the same meaning as commonly understood by those having ordinary skill in the art. Terms such as those defined in generally used dictionaries will be interpreted to have the meaning consistent with the meaning in the context of the related art, and will not be interpreted as an ideal or excessively formal meaning unless expressly defined in the present invention.

<Tandem Catalyst for Synthesizing Methyl Acetate from Carbon Dioxide>

FIG. 1 is a view schematically showing a tandem catalyst for synthesizing methyl acetate from carbon dioxide according to one embodiment of the present invention.

Referring to FIG. 1, the tandem catalyst for synthesizing methyl acetate from carbon dioxide according to one embodiment of the present invention may include a first catalyst including nano-ferrierite (N-FER) zeolite, and a second catalyst having a core-shell structure including a composite metal oxide core and a silica shell surrounding a surface of the composite metal oxide core.

The first catalyst may include nano-ferrierite (N-FER) zeolite, and arranged in tandem with the second catalyst in a dual-bed form, so as to be applied as a catalyst for producing methyl acetate from carbon dioxide in a single step.

In one embodiment, the nano-ferrierite (N-FER) zeolite may be Na-type ferrierite or H-type ferrierite, and may have a Si/Al molar ratio of 10 to 20 and a BET surface area of 290 $m^2/g$ to 350 $m^2/g$. In addition, the first catalyst may have a size of 200 nm to 800 nm. The first catalyst may have the above nano size to increase the surface area of the catalyst, so that the activity of the catalyst may be increased, and may have high methyl acetate (MA) selectivity, high carbon dioxide conversion and high stability, so that excellent catalytic performance can be exhibited.

The second catalyst may have a core-shell structure including a composite metal oxide core and a silica shell surrounding a surface of the composite metal oxide core, and may be arranged in tandem with the first catalyst in a dual-bed form so as to be applied as a catalyst for producing methyl acetate from carbon dioxide in a single step.

In one embodiment, the composite metal oxide core may include copper oxide (CuO) and zinc oxide (ZnO). Due to the core-shell structure in which the composite metal oxide core is surrounded by the silica shell, the complex metal oxide as an active material can be prevented from being deactivated.

In one embodiment, the second catalyst may include 2 wt % to 10 wt % of copper oxide (CuO), 1 wt % to 5 wt % of zinc oxide (ZnO) and a remainder of the silica shell based on total weight. When the copper oxide and the zinc oxide content exceed the above contents, the activity of the catalyst may be decreased due to the small amount of active metal, or the activity of the catalyst may be decreased because the structure of the silica shell collapses due to the large amount of composite metal oxide core.

In one embodiment, the composite metal oxide core of the second catalyst has a size of 5 nm to 10 nm, and the silica shell may have a diameter of 20 nm to 50 nm. The composite metal oxide core may have a size of 5 nm to 10 nm, so that deactivation may be prevented.

In addition, in the tandem catalyst, the weight ratio of the second catalyst/the first catalyst may be 0.1 to 2.0. When the weight ratio is less than 0.1, hydrocarbon instead of methyl acetate may be a main product through an additional side reaction. When the ratio exceeds 2.0, an acid site is insufficient, and accordingly, the methanol formed by the first catalyst may not be completely converted to DME.

In the tandem catalyst system of the present invention, a selective conversion reaction from carbon dioxide to methyl acetate may be performed. In other words, the tandem catalyst of the present invention may be used in a single step of synthesizing methyl acetate from carbon dioxide. The conventional synthesis of methyl acetate from carbon dioxide is performed through multiple synthesis processes other than the single process. However, when the tandem catalyst according to the present invention is used, carbon dioxide may be converted into oxygenate (methanol/dimethyl ether) and carbon monoxide, which participate in a carbonylation reaction through a reverse water gas shift (RWGS) reaction, so that, ultimately, a single-step methyl acetate synthesis process can be realized.

The tandem catalyst according to the present invention may activate inert carbon dioxide to realize a controllable oxygenate (methanol, dimethyl ether)/carbon monoxide formation ratio, so that methyl acetate may be selectively produced by successive gas-phase carbonylation events, and side reactions such as hydrocarbon formation may be suppressed in conditions of significant carbon monoxide yield due to the RWGS reaction.

In other words, the tandem catalyst according to the present invention may have high methyl acetate selectivity, high $CO_2$ conversion and high stability, so that excellent catalytic performance can be exhibited. Thus, the tandem catalyst according to the present invention may produce methyl acetate serving as an essential intermediate in ethanol synthesis from carbon dioxide as greenhouse gas through only the single step, so that carbon neutrality can be realized. As a result, when carbon dioxide is converted to methyl acetate (MA) in the related art, a carbonylation reaction from $CO_2$ into methanol, methanol into DME, and DME and CO into MA is performed through multiple processes. However, the present invention integrates the multiple processes into one process, so that low energy consumption for producing methyl acetate (MA) can be implemented, enormous economic benefits can be obtained, and significant production for achieving carbon neutrality can be implemented by utilizing greenhouse gases.

<Method for Preparing Tandem Catalyst for Synthesizing Methyl Acetate from Carbon Dioxide>

The method for preparing a tandem catalyst for synthesizing methyl acetate from carbon dioxide according to one embodiment of the present invention may include: a first step S100 of preparing nano-ferrierite (N-FER) zeolite by hydrothermally synthesizing a first precursor solution containing a first silica precursor, an alumina precursor and a first organic template agent and then calcining; a second step S200 of preparing a composite metal oxide core-silica shell by adding a second silica precursor solution to a second precursor solution containing a metal precursor and a second organic template agent and then calcining; and a third step S300 of arranging the nano-ferrierite (N-FER) zeolite and the composite metal oxide core-silica shell in tandem.

Step S100 is a step of preparing nano-ferrierite (N-FER) zeolite by hydrothermally synthesizing a first precursor solution containing a first silica precursor, an alumina precursor and a first organic template agent and then calcining.

In one embodiment, the first silica precursor may include silica sol, tetraethyl orthosilicate (TEOS), fumed silica, colloidal silica, silica gel, sodium silicate, or a combination thereof, but the present invention is not limited thereto.

In one embodiment, the alumina precursor may include aluminum oxide, kaolin, aluminum isopropoxide, aluminum nitrite, sodium aluminate, aluminum sulfate, or a combination thereof, but the present invention is not limited thereto.

In addition, the first organic template agent serves as a structural direct agent (SDA) to establish initial organic-inorganic interactions for crystallization of nano-ferrierite (N-FER) zeolites. In other words, the first organic template agent may play an important role as a structural direct agent (SDA) for forming a ferrierite framework as an organic compound having a specific nitrogen-containing heterocyclic compound structure. Specifically, the first organic template agent serves as a template and a pore filler through a strong structure-inducing effect during crystallization of ferrierite. This is due to organic molecules that can lead to the formation of several zeolite structures.

The first organic template agent may include cetrimonium bromide, ammonium lauryl sulfate, pyridine, pyrrolidine, ethylenediamine, n-butylamine, or a combination thereof, but the present invention is not limited thereto. In one embodiment, the first organic template agent may be included by about 5 wt % to about 20 wt % based on a total weight of the first precursor solution, and the molar ratio of the first silica precursor and the first organic template may be 0.5:1 to 2:1. When the content of the first organic template agent deviates from the above weight range, it may cause incomplete crystallization.

In addition, N-FER zeolite having various Si/Al molar ratios may be synthesized by adjusting the amount of precursor material in the first precursor solution of the present invention. For example, the first silica precursor and the alumina precursor may have a molar ratio of about 5:1 to about 20:1.

In addition, the first precursor solution may be prepared by adding and mixing the first silica precursor, the alumina precursor and the first organic template agent to a basic aqueous solution. The basic aqueous solution may include alkaline hydroxide aqueous solution including sodium hydroxide, potassium hydroxide, magnesium hydroxide, or a combination thereof.

In one embodiment, the first precursor solution may be prepared by dissolving a basic aqueous solution in water, mixing and stirring the dissolved basic aqueous solution with a first silica precursor at room temperature for about 30 minutes to about 2 hours, adding a first organic template agent and stirring for about 6 hours to about 18 hours, and adding an alumina precursor and stirring for about 6 hours to about 18 hours.

In addition, according to one embodiment of the present invention, nano-ferrierite (N-FER) zeolite may be prepared by hydrothermally synthesizing the first precursor solution and then calcining. The hydrothermally synthesizing may be performed at 110° C. to 180° C. for 168 hours to 504 hours. When the hydrothermally synthesizing temperature is less than 110° C., a tendency similar to reduced crystallization time less than 168 hours may be exhibited due to defective crystallization. When the hydrothermally synthesizing temperature exceeds 180° C., a tendency similar to crystallization time exceeding 504 hours may be exhibited due to increase in crystal size of ferrierite (FER).

After Na-type ferrierite zeolite obtained after the hydrothermal synthesis is washed and dried, calcining may be additionally performed at a temperature of about 450° C. to about 650° C. for about 6 hours to remove the first organic template agent. When the calcining temperature is less than 450° C., the residual first organic template agent may block a pore structure of Na-type ferrierite, and when the calcining temperature exceeds 650° C., collapse of the ferrierite framework structure may occur.

In addition, the present invention further includes, after step S100, performing ion exchange by dispersing the synthesized nano-ferrierite (N-FER) zeolite in an ammonium solution; and calcining the ion exchanged nano-ferrierite (N-FER) zeolite at 450° C. to 650° C., so that H-type ferrierite zeolite may be prepared.

In one embodiment, the step of performing ion exchange may be repeated about 3 times to about 6 times. Na-type ferrierite may be converted to $NH_4^+$-type ferrierite through the ion exchange, and the $NH_4^+$-type ferrierite may be obtained after washing and drying.

In addition, the calcining step is a step for converting $NH_4^+$-type ferrierite into H-type ferrierite. For example, when $NH_4^+$-type ferrierite is calcined at 450° C. to 650° C. for about 3 hours, $NH_4^+$-type ferrierite may be converted to H-type ferrierite as $NH_3$ is decomposed and removed. When the calcining temperature is less than 450° C., When the calcining temperature exceeds 650° C., collapse of the ferrierite framework structure may occur.

Step S200 is a step of preparing a composite metal oxide core-silica shell by adding a second silica precursor solution to a second precursor solution containing a metal precursor and a second organic template agent and then calcining. Step S200 may be performed simultaneously with step S100 or performed before/after step S100, and the present invention may not be limited to the sequence.

In one embodiment, the second precursor solution may be prepared by mixing a first solution containing a metal precursor with a second solution containing a second organic template agent.

The metal precursor contained in the first solution refers to a material for forming a composite metal oxide core serving as an active material of a catalyst. In one embodiment, the metal precursor used in the present invention may include a copper precursor and a zinc precursor. More specifically, the copper precursor may include copper acetate, copper chloride, copper nitrate, or a combination thereof, and the zinc precursor may include zinc acetate, zinc chloride, zinc nitrate or a combination thereof, but the present invention is not limited thereto.

In one embodiment, the first solution may be prepared by dissolving a metal precursor material in a solvent such that the metal precursor has a concentration of about 0.1 mol/L to about 3.0 mol/L in the first solution. The concentration of the first solution may be defined as a sum of moles of copper and zinc. In one embodiment, the copper precursor and the zinc precursor may contain copper and zinc in amounts of 2 wt % to 10 wt % and 1 wt % to 5 wt %, respectively, based on a total weight of the catalyst. In addition, water, ethanol or acetone may be used as a solvent for preparing the first solution.

The second organic template agent contained in the second solution serves as a template for forming the core-shell structure of the catalyst. Specifically, a chemical bond may proceed in core metal with a hydrophilic portion of the second organic template agent, and a chemical bond may proceed in silica with a hydrophobic portion of the second organic template agent, thereby forming the catalyst having the core-shell structure. The above second organic template material may include cetrimonium bromide (CTAB), ethylene oxide-propylene oxide-ethylene oxide copolymer (EO106PO70EO106), polyoxyethylene (10) cetyl ether (C16E10), ethylene oxide-propylene oxide-ethylene oxide copolymer (EO20PO70EO20), polyethylene glycol hexadecyl ether ($C_{16}H_{33}(OCH_2CH_2)nOH$, n=1 to 10) or a combination thereof, but the present invention is not limited thereto.

In one embodiment, the second solution may be prepared by dissolving the second organic template agent in a solvent such that the second organic template material has a weight ratio of about 5 wt % to about 50 wt % in the solvent, and then stirring the dissolved second organic template agent at 500 rpm to 1000 rpm at a temperature of about 30° C. to about 70° C. for about 2 hours to about 12 hours. Benzene, toluene, ethylbenzene, cyclohexane, hexane, or a combination thereof may be used as the solvent for preparing the second solution.

In addition, the second precursor solution may be prepared by dropping the first solution into the second solution, dropping the second solution into the first solution, or simultaneously dropping the first solution and the second solution. In one embodiment, the second precursor solution may be prepared by adding the first solution to the second solution at 30° C. to 70° C. and stirring, and the mixture may be additionally stirred for 30 minutes to 2 hours to form a homogeneous solution.

The second silica precursor solution includes a second silica precursor material for forming the silica shell of the catalyst, and may include silica sol, tetraethyl orthosilicate, well dispersed fumed amorphous silica or a combination thereof. The second silica precursor may be added in an amount of about 80 wt % to about 98 wt % based on a weight of a final catalyst. In addition, the second silica precursor solution may include ammonium aqueous solution, ammonium carbonate solution, or a combination thereof to maintain an alkaline condition.

In addition, in Step S200, the second silica precursor solution may be added to the second precursor solution, the mixed solution may be stirred for 30 minutes to 4 hours, and then the mixed solution may be additionally heated at about 30° C. to about 70° C. and 20 rpm to 1000 rpm for 1 hour to 5 hours. After the above step, a finally precipitated solution may be centrifuged with an ethanol solution and then dried at 60° C. to 100° C. for 10 hours to 24 hours to obtain dry powder.

Thereafter, a composite metal oxide core-silica shell may be prepared by calcining the dried powder. The calcining is configured to remove the second organic template agent and form a pore structure and a metal oxide active site for the hydrogenation reaction of the catalyst. In one embodiment, the calcining may be performed at about 400° C. to about 600° C. for 2 hours to 5 hours. When the calcining temperature is less than 400° C., pores may be blocked and copper-zinc oxide nanoparticles may be insufficiently formed because the second organic template agent may not be completely removed. In addition, when the calcining temperature exceeds 600° C., the structure of the silica shell may collapse.

S300 step is a step of arranging the nano-ferrierite (N-FER) zeolite and the composite metal oxide core-silica shell in tandem. Catalysts may be integrated into parts, respectively, and arranged in tandem in a dual-bed form, so that the tandem catalyst capable of synthesizing methyl acetate from carbon dioxide in a single step may be prepared.

<Method for Preparing Methyl Acetate from Carbon Dioxide>

The method for preparing methyl acetate from carbon dioxide according to one embodiment of the present invention includes: arranging a tandem catalyst of the present invention inside a reactor; reducing the tandem catalyst by primarily heating the inside of the reactor; and performing a reaction by injecting gas containing carbon dioxide and hydrogen into the reactor, so that methyl acetate may be synthesized from carbon dioxide.

In one embodiment, a fixed bed reactor may be used for the reactor, but the present invention is not limited thereto. In addition, the tandem catalyst may be arranged inside the fixed bed reactor in a dual-bed form.

In one embodiment, the heating may be performed at 200° C. to 400° C. For example, in the step of reducing the tandem catalyst, a temperature may be raised to a reduction temperature at about 5° C./min and maintained for about 1 hour to 3 hours while flowing 5 vol % of hydrogen-nitrogen-mixed gas inside the reactor, so that the tandem catalysts may be reduced.

In one embodiment, in the step of performing the reaction, the reaction may be performed at 200° C. to 400° C. For example, the reaction may be performed at a temperature of 200° C. to 400° C. while injecting gas containing carbon dioxide and hydrogen. In one embodiment, the gas containing carbon dioxide and hydrogen may contain hydrogen and carbon dioxide in the molar ratio of 1:1 to 5:1, and may include 6 mol % to 48 mol % of carbon dioxide based on a total amount of the mixed gas.

Hereinafter, the present invention will be further described with reference to specific Examples.

Preparation Example

[Preparation of N-FER Catalyst]

An alkaline hydroxide solution is prepared, mixed with TEOS as a silica source and stirred at room temperature for 1 hour, and then pyrrolidine as an organic template agent is added and additionally stirred for 11 hours. Thereafter, $NaAlO_2$ as an alumina source is added and additionally stirred for 12 hours. An N-FER catalyst having a Si/Al molar ratio of 10 to 20 may be synthesized by adjusting relative amounts of the sources. The precursor solution prepared in the above manner is transferred to a Teflon-lined stainless steel autoclave and hydrothermally synthesized at 140° C. for 14 days.

After crystallization is complete, the obtained precursor is washed with distilled water (DI water) and dried at 60° C. to 110° C. overnight. The dried precursor is calcined at 550° C., thereby obtaining Na-type FER. The obtained Na-type FER is dispersed in ammonium nitrate ($NH_4NO_3$) solution and maintained at 80° C. for 3 hours to perform ion exchange. Thereafter, filtration and washing are performed and then drying is performed at 60° C. to 110° C. overnight. Finally, the ion-exchanged sample is calcined at 550° C., thereby obtaining H-type N-FER.

[Preparation of CZ@$SiO_2$ Catalyst]

Solution A may be prepared by dissolving copper(II) nitrate trihydrate (99.0%, Daejung) and zinc nitrate hexahydrate (98%, Sigma-Aldrich) in water, so that copper and zinc have the molar ratio of 7:3 and have a sum of 0.5 M therebetween at room temperature.

Solution B may be prepared by dissolving 10.5 g of an organic template agent Brij C10 (polyethylene glycol hexadecyl ether having an average molecular weight of 683 or less, Sigma-Aldrich) in 50 ml of cyclohexane (99.5%, Samcheon) as a solvent at a temperature of 50° C. for 6 hours.

The concentration of solution A is 0.5 M and the concentration of solution B is 0.21 g/mL. Thereafter, the prepared solution A is added to solution B while stirring at 50° C. for 1 hour.

Thereafter, 3 ml of ammonia water ($NH_4OH$, 25% to 30%, Deoksan) and 5 ml of a solution C of tetraethyl orthosilicate (TEOS, 98.5%, Daejeong Chemical) as a silica precursor are added to the mixed solution while stirring and additionally maintained for 2 hours. Thereafter, a final product is collected in 30 mL of ethanol. The collected sample is dried at 80° C. overnight and calcined at 550° C. for 2 hours.

Example 1: Preparation of Catalyst 1

The prepared CZ@$SiO_2$ is used in a first catalyst layer and N-FER is used in a second catalyst layer, so that a tandem catalyst is prepared.

Example 2: Preparation of Catalyst 2

The prepared CZ@$SiO_2$ is used in a first catalyst layer, and FER zeolite commercially available from Vision Chemical Co., is used in a second catalyst layer, so that a tandem catalyst is prepared.

Comparative Example 1: Preparation of Catalyst 3

The prepared CZ@$SiO_2$ is used in a first catalyst layer, and mordenite zeolite commercially available from Alfa Aesar Co., is used in a second catalyst layer, so that a tandem catalyst is prepared.

Example 3: Preparation of Catalyst 4

First, 0.6 g of $Zn(NO_3)_2 \cdot 6H_2O$ and 5.8 g of $Zr(NO_3)_4 \cdot 5H_2O$ are dissolved in 100 ml of distilled water in a flask. A precipitate of 3.06 g of $(NH_4)_2CO_3$ in 100 ml of an aqueous solution is added to the solution while vigorously stirring at 70° C. The suspension is continuously stirred at 70° C. for 2 hours, cooled to room temperature, filtered, and washed three times with distilled water. The collected sample is dried at 110° C. for 4 hours and calcined at 500° C. for 3 hours in air atmosphere. This is named ZnZrOx. ZnZrOx prepared according to the above scheme is used as a first catalyst layer, and the prepared N-FER (NFER) is used in a second catalyst layer, so that a tandem catalyst is prepared.

Example 4: Preparation of Catalyst 5

Copper nitrate, zinc nitrate and aluminum nitrate are dissolved in distilled water (DI Water) so that the molar ratio of Cu:Zn:Al is 7:3:1, thereby preparing a metal precursor and ammonium carbonate precipitant solution. Coprecipitation is performed in 200 mL of distilled water (DI Water) at 70° C. while stirring. An individual metal precursor and precipitant solution is added while maintaining pH of the solution at about 7. The mixed slurry solution including the different forms of FER is additionally stirred at 70° C. for 1 hour and then the solution is filtered. The collected sample is dried overnight and then calcined at 350° C. for 3 hours in an air atmosphere. This is named Cu—ZnO—Al2O3 (CZA). CZA prepared according to the above scheme is used in a first catalyst layer, and the prepared N-FER (NFER) is used in a second catalyst layer, so that a tandem catalyst is prepared.

Table 1 briefly shows structures of the tandem catalysts 1 to 5 prepared according to Examples 1 to 4 and Comparative Example 1 as below.

TABLE 1

| Item | First catalyst layer | Second catalyst layer |
|---|---|---|
| Example 1 | CZ@$SiO_2$ | N-FER |
| Example 2 | CZ@$SiO_2$ | Commercial FER zeolite |
| Comparative Example 1 | CZ@$SiO_2$ | Commercial mordernite zeolite |

TABLE 1-continued

| Item | First catalyst layer | Second catalyst layer |
|---|---|---|
| Example 3 | ZnZrOx | N-FER |
| Example 4 | Cu—ZnO—$Al_2O_3$ | N-FER |

Experimental Example 1: Structural Analysis of Catalysts

1) X-Ray Diffraction Pattern (XRD) Analysis

XRD analysis is performed on the N-FER catalyst and the CZ@$SiO_2$ catalyst of the tandem catalyst according to Example 1 of the present invention, and the commercial FER zeolite catalyst as the second layer catalyst of the tandem catalysts according to Comparative Example 1, and the results are shown in FIG. 2.

Based on the XRD analysis results in FIG. 2, it can be seen that only peaks corresponding to ferrierite are detected and peaks corresponding to copper or zinc are not detected, and it can be seen that the copper and zinc nanoparticles are well dispersed because only amorphous $SiO_2$ is observed.

2) X-Ray Fluorescence (XRF) Analysis

X-ray fluorescence analysis is performed on the N-FER catalyst and the CZ@$SiO_2$ catalyst of the tandem catalyst according to Example 1 of the present invention, and the commercial FER zeolite catalyst as the second layer catalyst of the tandem catalysts according to Comparative Example 1 to analyze mass contents of CuO, ZnO, $Al_2O_3$ and $SiO_2$, and the results are shown in Table 2 as below.

TABLE 2

| Catalyst name | Experiment Example, XRF | | | | Molar ratio | |
|---|---|---|---|---|---|---|
| | CuO (wt %) | ZnO (wt %) | $Al_2O_3$ (wt % ) | $SiO_2$ (wt %) | Cu/ Zn | Si/ Al |
| N-FER | — | — | 93.15 | 6.85 | — | 11.5 |
| Commercial FER zeolite | — | — | 92.59 | 7.41 | — | 10.6 |
| CZ@$SiO_2$ | 4.41 | 1.86 | 93.73 | — | 2.43 | — |

Referring to Table 2, it can be confirmed of actual compositions of the catalysts. It is confirmed that the Si/Al molar ratios on XNFER and CFER are 11.5 and 10.6, respectively. For CZ@$SiO_2$, it is confirmed that the Cu/Zn molar ratio is 2.43 and the weight ratio of CuO and ZnO are 4.41 wt % and 1.86 wt %, respectively.

3) Nitrogen Adsorption/Desorption Analysis ($N_2$-Physisorption)

Specific surface areas and pore volumes are analyzed through nitrogen adsorption and desorption analysis to analyze surface structures of the catalysts. In order to remove moisture and surface-adsorbed substances, continuous heat treatments are performed under vacuum conditions at 90° C. for 1 hour and 350° C. for 4 hours, and then nitrogen is adsorbed and desorbed under isothermal conditions of −196° C. The results are shown in FIG. 3 and Table 3 below.

TABLE 3

| Catalyst name | BET Surface Area ($m^2$/g) | Pore Volume ($cm^3$/g) |
|---|---|---|
| N-FER | 299.8 | 0.19 |
| Commercial FER zeolite | 272.6 | 0.12 |
| CZ@$SiO_2$ | 101.7 | 0.38 |

Referring to Table 3, it can be seen that N-FER exhibits a higher BET surface area (299.8 $m^2$/g) compared to commercial FER zeolite (272.6 $m^2$/g), and it can be confirmed that a similar tendency in pore volumes, in which N-FER has more pores. This is one of the reasons why N-FER exhibits an activity response higher than that of commercial FER zeolite. In addition, for CZ@$SiO_2$, it is confirmed that the BET surface is 101.7 $m^2$/g and the pore volume is 0.38 $cm^3$/g.

4) Transmission Electron Microscopy (TEM) Analysis

Images are obtained through transmission electron microscopy analysis of the catalysts, and the results are shown in FIG. 4.

Referring to FIG. 4, it can be confirmed that N-FER synthesized according to the Example of the present invention has a nanoscale crystal size of 200 nm to 800 nm.

Experimental Example 2: Ammonia Adsorption/Desorption Analysis ($NH_3$-Chemisoption)

$NH_3$-TPD analysis is performed to analyze an acid site of the N-FER catalyst synthesized according to the Example of the present invention, and the results are shown in FIG. 5. $NH_3$ molecules is used as probes to measure acid sites, so that the amount and intensity of acid sites are measured. $NH_3$ is adsorbed at 100° C. and then desorbed after raising the temperature to 800° C. FIG. 5 and Table 4 show quantitative amounts through the analysis as below.

TABLE 4

| Catalyst name | Weak/Medium/strong (mmol/g) | Total (mmol/g) |
|---|---|---|
| N-FER | 0.464/0.235/0.490 | 1.189 |
| Commercial FER zeolite | 0.631/0.309/0.29 | 1.230 |

Referring to Table 4, it can be confirmed of $NH_3$-TPD results on N-FER and commercial FER zeolite catalysts. The slightly acidic and moderately acidic sites of N-FER are lower than those of commercial FER zeolite; The strongly acidic site of N-FER is higher than that of commercial FER zeolite. In other words, it is confirmed that high acidity of an 8-membered ring of N-FER may lead to higher MA production.

Experimental Example 3: Synthesis Conversion Reaction Experiment on Methyl Acetate from Carbon Dioxide and Hydrogen First, 0.2 g of CZ@$SiO_2$ and 1.4 g of NFER are arranged in a dual-bed form and reacted in a ⅜ inch fixed bed reactor. Before the reaction, a temperature is raised to 300° C. at 5° C./min while 5 vol % of $H_2/N_2$ gas being flowed at a volume flow rate of 30 cm3/min, and reduction is performed for 2 hours. Next, after purging with reaction gas at the ratio of carbon dioxide:hydrogen:nitrogen (internal standard substance)=24:72:4, a pressure is increased to 50 bar. While the gas is injected with a flow rate at a space velocity SV of 2,500 mL/gcat·h, a reaction is carried out at 300° C. FIG. 1 shows the corresponding dual-bed form.

Products for tail gas are analyzed by online gas chromatography, and the obtained compositions are used to calculate the product distribution (selectivity and productivity) as well as the $CO_2$ conversion. The $CO_2$ conversion and the product selectivity are calculated as average values from maximum points to last points in the stream. FIG. 6 and Table 5 below show results of the synthesis conversion reaction experiment on methyl acetate from carbon dioxide.

TABLE 5

| Examples/ Comparative Example | $CO_2$ Conv. (%) | CO Sel. (%) | CO-free selectivity (%) Hydro-carbons | MeOH | DME | MA |
|---|---|---|---|---|---|---|
| Example 1 | 19.7 | 55.3 | 26.0 | 11.0 | 12.2 | 50.8 |
| Example 2 | 19.3 | 69.3 | 77.1 | 0 | 1.6 | 21.3 |
| Comparative Example 1 | 16.0 | 54.4 | 100 | — | — | — |
| Example 3 | 9.2 | 14.3 | 67.4 | 8.4 | 7.6 | 16.1 |
| Example 4 | 30.2 | 64.7 | 23.1 | 14.6 | 17.0 | 45.3 |

Table 5 shows results on the carbon dioxide reaction experiment of Examples 1 to 4 and Comparative Example 1. It is conformed that, when N-FER (Example 1) is used in the second catalyst layer, the $CO_2$ conversion rate and the MA selectivity higher than when commercial FER zeolite (Example 2) and commercial modernite zeolite (Comparative Example 1) are used. In addition, it can be clearly seen that metal oxide is an essential element for selective MA production when compared using CZ@$SiO_2$ (Example 1), ZnZrOx (Example 3) and Cu—ZnO—$Al_2O_3$(Example 4) in the first catalyst layer. The ZnZrOx catalyst exhibits very low MA selectivity due to low CO production from RWGS under reaction conditions. In the case of Cu—ZnO—Al2O3 catalyst, higher $CO_2$ conversion compared to CZ@$SiO_2$ is accompanied by formation of more water despite sufficient CO production from RWGS. Accordingly, it can be seen that this exerts a negative impact on MA conversion. Thus, it is confirmed that the best activity are exhibited since the $CO_2$ conversion and the MA selectivity are highest when CZ@$SiO_2$ and N-FER are used as the first and second catalyst layers, respectively, in the methyl acetate reaction through direct conversion of carbon dioxide.

Although the present invention has been described with reference to exemplary embodiments, it will be apparent to a person having ordinary skill in the art that various modifications and variations can be made in the present invention without departing from the scope and field of the following appended claims.

What is claimed is:

1. A tandem catalyst for synthesizing methyl acetate from carbon dioxide, the tandem catalyst comprising:
a first catalyst including nano-ferrierite (N-FER) zeolite; and
a second catalyst having a core-shell structure including a composite metal oxide core and a silica shell surrounding a surface of the composite metal oxide core.

2. The tandem catalyst of claim 1, wherein the second catalyst/the first catalyst have a weight ratio of 0.1 to 2.0.

3. The tandem catalyst of claim 1, wherein the composite metal oxide core includes copper oxide (CuO) and zinc oxide (ZnO).

4. The tandem catalyst of claim 3, wherein the second catalyst includes 2 wt % to 10 wt % of copper oxide (CuO), 1 wt % to 5 wt % of zinc oxide (ZnO) and a remainder of the silica shell based on total weight.

5. The tandem catalyst of claim 1, wherein the nano-ferrierite (N-FER) zeolite is Na-type ferrierite or H-type ferrierite, and the nano-ferrierite (N-FER) zeolite has a Si/Al molar ratio of 10 to 20 and a BET surface area of 290 $m^2/g$ to 350 $m^2/g$.

6. The tandem catalyst of claim 1, wherein the first catalyst has a size of 200 nm to 800 nm.

7. The tandem catalyst of claim 1, wherein the composite metal oxide core of the second catalyst has a size of 5 nm to 10 nm, and the silica shell has a diameter of 20 nm to 50 nm.

8. A method for preparing a tandem catalyst for synthesizing methyl acetate from carbon dioxide, the method comprising:
a first step of preparing nano-ferrierite (N-FER) zeolite by hydrothermally synthesizing a first precursor solution containing a first silica precursor, an alumina precursor and a first organic template agent and then calcining;
a second step of preparing a composite metal oxide core-silica shell by adding a second silica precursor solution to a second precursor solution containing a metal precursor and a second organic template agent and then calcining; and
a third step of tandem-arranging the nano-ferrierite (N-FER) zeolite and the composite metal oxide core-silica shell.

9. The method of claim 8, wherein the first silica precursor includes a substance selected from silica sol, tetraethyl orthosilicate (TEOS), fumed silica, colloidal silica, silica gel, and sodium silicate, the alumina precursor includes a substance selected from aluminum oxide, kaolin, aluminum isopropoxide, aluminum nitrite, sodium aluminate, and aluminum sulfate, and the first organic template agent includes a substance selected from cetrimonium bromide, ammonium lauryl sulfate, pyridine, pyrrolidine, ethylenediamine and n-butylamine.

10. The method of claim 8, wherein the first silica precursor and the first organic template agent have a molar ratio of 0.5:1 to 2:1, and the first silica precursor and the alumina precursor have a molar ratio of 5:1 to 20:1.

11. The method of claim 8, wherein, in the first step, the hydrothermally synthesizing is performed at 110° C. to 180° C. for 168 hours to 504 hours, and the calcining is performed at 450° C. to 650° C.

12. The method of claim 8, further comprising, after the first step:
performing ion exchange by dispersing the synthesized nano-ferrierite (N-FER) zeolite in an ammonium solution; and
calcining the ion exchanged nano-ferrierite (N-FER) zeolite at 450° C. to 650° C.

13. The method of claim 8, wherein the metal precursor includes a copper precursor and a zinc precursor, the second organic template agent includes a substance selected from cetrimonium bromide (CTAB), ethylene oxide-propylene oxide-ethylene oxide copolymer (EO106PO70EO106), polyoxyethylene (10) cetyl ether (C16E10), ethylene oxide-propylene oxide-ethylene oxide copolymer (EO20PO70EO20) and polyethylene glycol hexadecyl ether ($C_{16}H_{33}(OCH_2CH_2)_nOH$, n=1 to 10), and the second silica precursor solution includes a substance selected from a basic material, and silica sol, tetraethyl orthosilicate (TEOS) and fumed amorphous silica as secondary silica precursors.

14. The method of claim 8, wherein, in the second step, the calcining is performed at 400° C. to 600° C.

15. A method for preparing methyl acetate from carbon dioxide, the method comprising:

arranging a tandem catalyst inside a reactor, the tandem catalyst comprising:

a first catalyst including nano-ferrierite (N-FER) zeolite; and a second catalyst having a core-shell structure including a composite metal oxide core and a silica shell surrounding a surface of the composite metal oxide core;

reducing the tandem catalyst by heating the inside of the reactor; and performing a reaction by injecting gas containing carbon dioxide and hydrogen into the reactor, so that methyl acetate is synthesized from carbon dioxide.

16. The method of claim 15, wherein the reaction is performed at 200° C. to 400° C.

17. The tandem catalyst of claim 1, wherein the first catalyst and the second catalyst are arranged in tandem, and form hydrocarbons, methanol (MeOH), dimethyl ether (DME), and methyl acetate (MA) from carbon dioxide.

* * * * *